United States Patent
Tashiro

[11] Patent Number: 5,958,450
[45] Date of Patent: *Sep. 28, 1999

[54] METHOD OF DRUG DELIVERY AND COATED ORAL DOSAGE FORMS FOR USE IN THE METHOD

[75] Inventor: Shintaro Tashiro, Kanagawan-ken, Japan

[73] Assignee: Phillip Peatey & Gunter Pauli, Kanagawen-ken, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/849,367

[22] PCT Filed: Dec. 5, 1995

[86] PCT No.: PCT/AU95/00821

§ 371 Date: Jun. 5, 1997

§ 102(e) Date: Jun. 5, 1997

[87] PCT Pub. No.: WO96/17599

PCT Pub. Date: Jun. 13, 1996

[30] Foreign Application Priority Data

Dec. 5, 1994 [JP] Japan .................................... 6-333235
May 31, 1995 [AU] Australia ...................................... 3280
Aug. 14, 1995 [JP] Japan .................................... 7-238933

[51] Int. Cl.⁶ .................................................. A61K 09/48
[52] U.S. Cl. ........................... 424/451; 424/456; 424/485
[58] Field of Search .................................... 424/479, 485, 424/451, 456; 514/32, 35, 54; 536/3

[56] References Cited

U.S. PATENT DOCUMENTS

| | | | |
|---|---|---|---|
| 2,801,203 | 7/1957 | Leb et al. | 424/479 |
| 3,406,031 | 10/1968 | Lee | 424/479 |
| 5,200,195 | 4/1993 | Dong et al. | 424/473 |
| 5,416,205 | 5/1995 | della Valle et al. | 514/54 |
| 5,629,003 | 5/1997 | Horstmaun et al. | 424/401 |

FOREIGN PATENT DOCUMENTS

| | | |
|---|---|---|
| 0651804 | 5/1991 | Australia . |
| 93/11748 | 6/1993 | WIPO . |

OTHER PUBLICATIONS

Behrens et al Tropical Doctor vol. 22 No. 3 pp. 107–108 1992.

News Release Aug. 21, 1987 p.1 Bepex Introduces New Food Grade Sodium Alginates.

Derwent Abstract No. 89–228916, JP 01–228916, "Seaweed–Filled Sheet", Satomitsu Kitamura, dated Sep. 12, 1989.

*Primary Examiner*—Neil S. Levy
*Attorney, Agent, or Firm*—Griffin, Butler, Whisenhunt & Szipl, LLP

[57] ABSTRACT

A coating for a drug wherein said coating is formed from seaweed and/or kelp, the seaweed and/or kelp being of a type which is impervious to gastric acidity but denaturable by alkali found in the intestines. Suitably, the coating comprises a capsule which also incorporates a binder or the coating may comprise barium sulfate or other acid-resistant bulking agents.

19 Claims, 2 Drawing Sheets

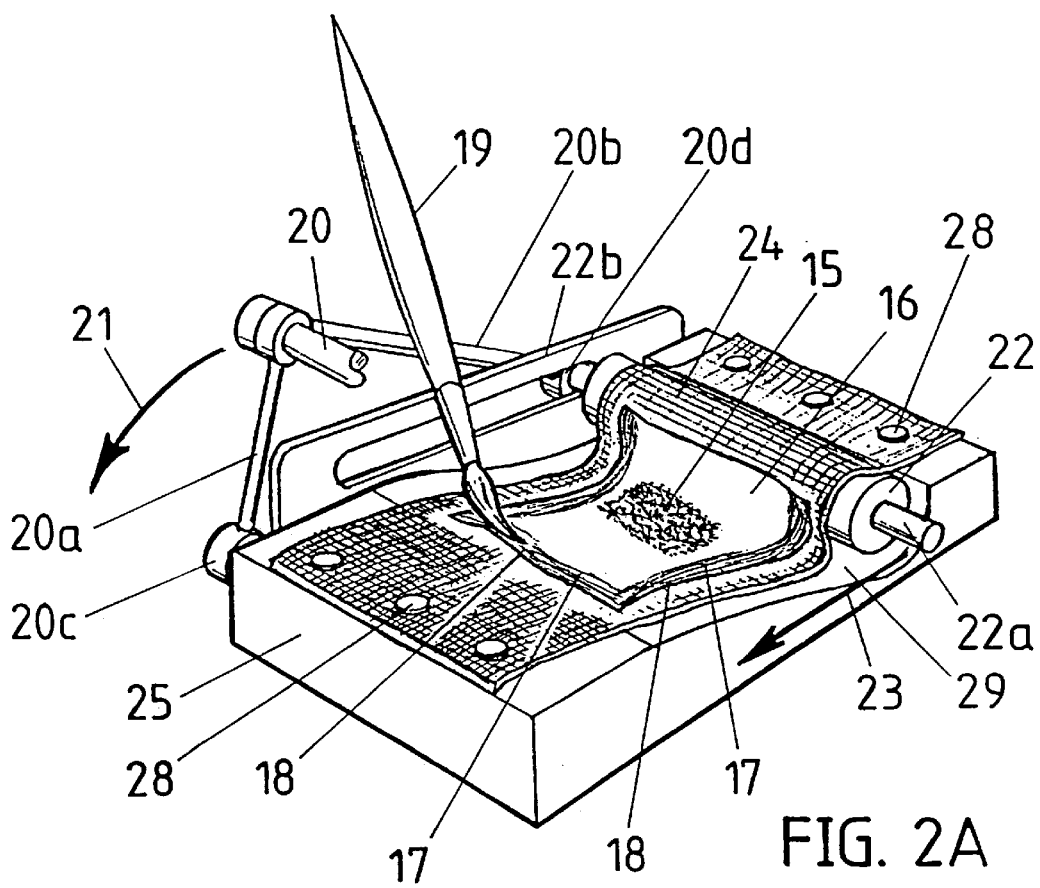
FIG. 2A
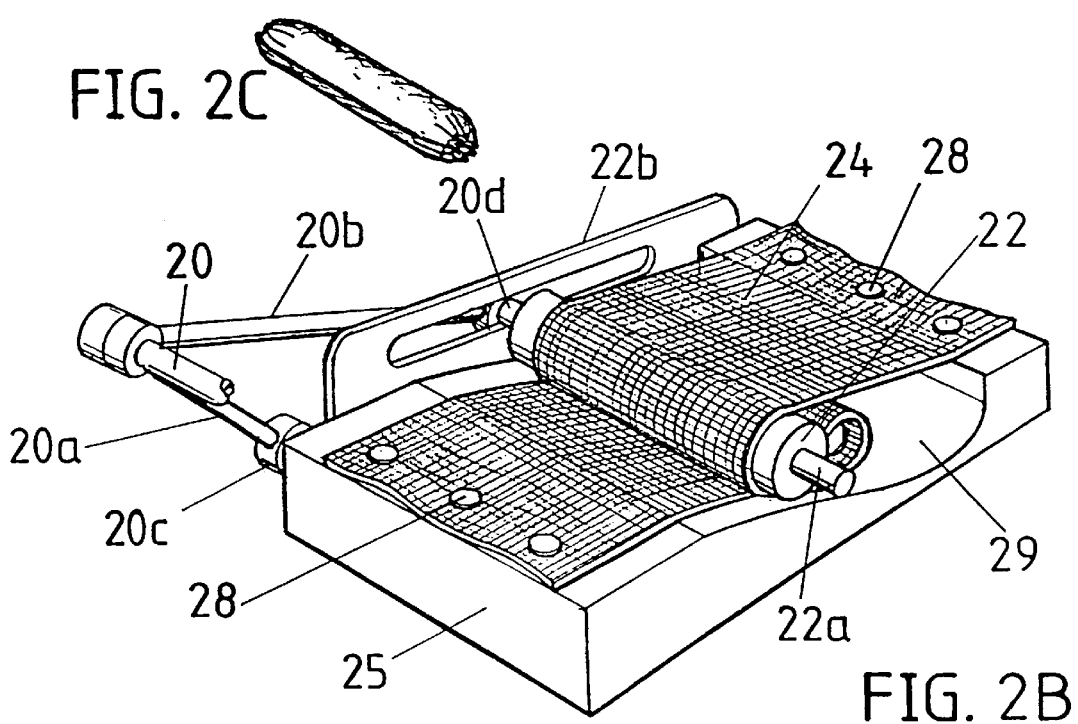
FIG. 2C
FIG. 2B 5,958,450

METHOD OF DRUG DELIVERY AND COATED ORAL DOSAGE FORMS FOR USE IN THE METHOD

FIELD OF THE INVENTION

THIS INVENTION relates to a method of drug delivery and coated oral dosage forms such as capsules for use in the method.

BACKGROUND OF THE INVENTION

In order to deliver drugs which may include medicines, vitamins and other substances directly to the intestines by oral means, such active substances are usually coated with gelatin based materials such as capsules or caplets. This is due to the fact that if such substances are not coated with a protective coating, such substances would be broken down in the highly acidic environment of the stomach.

Capsules are usually made in rigid or soft form wherein powders or granules of a drug or other active ingredient are enclosed in a rigid gelatin shell or in soft gelatin shell which soft shell may also contain glycerol as well as gelatin to maintain plasticity of the outer shell. Powder semi-solids or liquids that do not soften or dissolve the gelatin shell can be enclosed. Powder and semi-solids can be encapsulated in a two part shell i.e. cap and body whereas liquids may be encapsulated in a capsule that is formed, fitted and heat sealed all in one operation using especially designed apparatus.

In addition to inert polymers that control drug diffusion, polymers can be designed to dissolve, swell, or degrade in a controlled manner, thereby releasing the incorporated drug. It is, however, necessary that the polymer be transformed into a water-soluble product that evokes no limiting toxic response if the spent product is not to be reclaimed. The drug is locked into a polymer matrix (i.e. a drug reservoir) before its transformation. The surface area of the polymer-drug mass, the drug concentration and solubility characteristics, and the rate of polymer transformation affect the rate at which the drug is delivered. The polymer structure undergoes a phase change during which it or its by-products are removed or eliminated from the body, either during drug release or when most of the drug is deployed.

The polymers investigated for such systems include polyesters, polyorthoesters, polyacids, hydrogels, celluloses, polypeptides, polyaminotriazoles, and albumin beads. Therapeutic agents investigated for delivery from polymeric matrices include narcotic antagonists (naloxone), steroids, antimalarials, insulin, enzymes, antibacterials, ophthalmic agents, vitamins and anticarcinogens.

Encapsulation with liposomes promotes the passage of drugs across cell-membrane barriers, prolongs plasma lifetime of drugs with short biological half-lives, and directs drug disposition. The aqueous compartments bounded by bimolecular lipid layers carry the drug-containing platform closer to the target site, thus providing higher concentrations than the usual systemic therapy. The quantity of the drug or agent administered can, therefore, be reduced considerably.

Active ingredients which are required to be released in different parts of the alimentary tract may be coated or packaged in materials which react differently with body fluids having varying pH values in different parts of the alimentary tract.

Coatings which resist the action of gastric acids but dissolve under the less acidic conditions in the duodenum and intestines are generically known as enteric coatings and are applied to capsules as well as tablets.

Although enteric capsules have been known since the end of the 19th century their development has not paralleled that of enteric-coated tablets. This has been mainly due to the difficulties in making enteric capsules completely resistant to gastric acids.

Gelatin-based capsules, however, may be made acid resistant by treating them with formaldehyde. This process has a disadvantage in that the chemical cross linkage changes to the gelatin as a result of the formaldehyde treatment can continue during a storage period resulting in an undesirable hardening of the capsules.

Furthermore, trace amounts of formaldehyde in foods and pharmaceuticals because of the toxic properties of this substance also raises problems with food and drug administration authorities.

Gelatin capsules may also be coated with a solution of cellacephate, as described in U.S. Pat. Nos. 2,491,475 and 2,575,789. Cellacephate is a composition consisting of a mixture of gelatin and an alkali metal salt of a partial ester of a polycarboxylic acid and a suitable cellulose ether. For example, a solution of sodium carbonate in which cellacephate was dissolved was mixed with gelatin. Capsules were then made from this mixture. U.S. Pat. No. 2,718,667 refers to enteric capsules prepared solely from an alkali metal salt of cellacephate.

Capsules produced by cellacephate/gelatin mixtures however have the unfortunate disadvantage of being somewhat unstable on storage because of the decomposition of the cellacephate which liberates acetic acid. This results in a brittle capsule which is less soluble in the intestines and markedly reduces product yield.

Derivatives of cellulose with enteric properties have also been developed. An example of this is U.S. Pat. No. 3,826,666 which refers to a preparation of enteric capsules from a mixture of gelatin and the alkali metal salt of hypromellose phthalate. This resulted in an effective yield of capsules of between 80% and 90%. Further, soft single piece capsules with an improved film strength have also been produced by a mixture of cellacephate and hypromellose phthalate with gelatin and the addition of casein and latex.

Enteric capsules produced from polymers not based on cellulose have also been developed. For example, JP 7310522 refers to a capsule prepared from a mixture of gelatin and acrylic copolymers. Commercial gelatin-based encapsulation of medicinal substances are disclosed in, for example, (i) HUT853800-A, which refers to capsules formed from an emulsion containing surfactant, antioxidant and an aqueous solution of alkali metal alginate;

(ii) U.S. Pat. No. 5,362,564, which refers to a seamless capsule containing a $C_2$–$C_6$ fatty acid ester of sucrose sandwiched between hydrophobic layers and a coating film formed from a ester soluble polyhydric alcohol;

(iii) JO4027352-A, which refers to an enteric soft capsule obtained from gelatin, a plasticiser film base and water-soluble polysaccharide cross-linked by calcium ions;

(iv) U.S. Pat. No. 5,204,111, which refers to a capsule containing a hydrophobic substance, an isobutylene viscous oil and a polyvalent alcohol film coating;

(v) U.S. Pat. No. 5,330,835, which refers to an alginate capsule formed from addition of an alginate solution to a polyvalent metal salt solution; and (vi) JP59036540-A, which refers to microcapsules formed from gelatin and gum arabic, sodium alginate or carrageenan wherein the microcapsules are coated with flour, starch, powdered fat, cellulose protein, inorganic salt, organic acid salt, amino acid and sugar.

In all the above mentioned prior art specifications relating to capsules, survival of the capsule in the digestive environment of the stomach is primarily a function of both the thickness and the resistance to gastric acids of the encapsulating material. However, such capsules required the employment of complex chemicals such as polymers such as those described above and thus the production of such capsules was expensive. Such expense was often exacerbated when it was necessary to also employ special additives such as agar, glycerine, pectin and various water soluble alcohols.

Other substances which have been used for formation of capsules include sucrose, starch, talcum powder, kanzo powder (liquorice powder), rubber, grape sugar, crystalline cellulose, lactose titanium dioxide, calcium carbonate, ammonium phthalate, cellulose and other associated cellulose derivatives, sorbitol, juran gum and polyvinyl alcohol.

Another major disadvantage of the manufacture of capsules was that such manufacture necessitated the use of expensive apparatus especially adapted for this purpose.

Another major disadvantage of the prior art capsules was that the above materials had a tendency to break down in the stomach and thus the solution of overcoming this problem was to increase the thickness of the capsule which, however, could not be universally applied in operation.

SUMMARY OF THE INVENTION

It therefore is an object of the present invention to provide a method of drug delivery which is effective in use and which may alleviate the disadvantages of the prior art.

The invention therefore, in one aspect, provides a an oral dosage form containing a drug for drug delivery incorporating a coating which is formed at least partly from seaweed and/or kelp or extracts derived from seaweed and/or kelp which is impervious to gastric acidity but denaturable by alkali found in the intestines.

Preferably the seaweed and/or kelp is bound by binder which is also impervious to gastric acid(s) but also denaturable by alkali formed in the intestines.

The drug may be dipped in the seaweed and/or kelp or extract derived from the seaweed and/or kelp. Preferably the coating may comprise a capsule as discussed hereinafter.

In a preferred form, a sheet is formed at least partly from seaweed and/or kelp also using the binder wherein the drug is retained within the capsule which is formed by a folding operation wherein adjacent parts of the sheet are bonded to each other by the binder.

The invention also provides a method of manufacture of the capsule which includes the steps of (i) placing a drug on the sheet formed from seaweed and/or kelp; (ii) folding said sheet to retain said drug within the confines of said sheet and (iii) sealing or bonding adjacent parts of said sheet with said binder.

In another arrangement, a capsule may be formed from capsule components which incorporate at least some seaweed and/or kelp also incorporating said binder wherein each capsule component is formed by extrusion, moulding or other suitable process and then each capsule component is attached to each other to form a complete shell with the drug retained within a hollow interior of the complete shell.

Suitably a complete shell is formed from two half shell components. Such a capsule is suitable for encapsulating drugs in the form of powders or semi-solids.

Alternatively, a capsule may be formed in one operation from seaweed and/or kelp at least in part. Liquid drugs, for example, may be encapsulated in the capsule that is formed in the single operation.

Suitably the seaweed or kelp comprises a preparation of seaweed or kelp of the genus laminaria known as "konbu" or "kombu" in Japanese or seaweed of the variety *undaria pinnatifada* also known as "wakame" in Japanese. However, it will be appreciated that the seaweed sheet may be formed from any other variety which may be pressed to form a dry film thickness as hereinafter described and which is suitable for this purpose.

Most preferably the seaweed or kelp is of the *shiraita konbu* variety, known in Japan as "white board kelp". More broadly a family of kelps known as macrosystis or sarcophycus may be used which include laminaria.

Suitably the binder or bonding agent is an alginate of an alkali metal such as sodium alginate solution or potassium alginate solution. The alginate may have a concentration of between 0.05% and 20% by weight in water. However, a preferred concentration is between 0.1% and 3%.

The alginate binder may operate between temperatures of 1° C. and 150° C. However the preferred temperature range for its use is between 10° C. and 30° C. as this does not result in damage to the drug to be encapsulated. Other alginates may be utilised inclusive of alginates of Fe, Ag, Sr, Al, Mn, Se, Ca, K or Zn.

Preferably in the method of the invention the drug is moulded into individual pellets which may be of any suitable shape such as cylindrical or spherical before being placed on the sheet in one embodiment as described which is an especially preferred embodiment. The pellets may also be wetted with the binder prior to being placed on the sheet or when the pellets are on the sheet.

The folding of the sheet may be effected by any suitable means such as by a manual operation wherein adjacent longitudinal edges of the sheet may be folded initially in a transverse or lateral direction and subsequently the ends of the folded sheet are further folded to form the capsule.

Alternatively, one end of the sheet may be wound in a rolling operation by suitable apparatus as hereinafter described.

The seaweed and/or kelp may be initially prepared for encapsulation of the drug by a process which may include the steps of:

(i) application of preservative to the seaweed or kelp which may include granular salt in the case of wakame or ash in the case of konbu;

(ii) washing of the seaweed or kelp to remove the preservative and other foreign matter;

(iii) immersion of the seaweed or kelp in water to allow absorption of water or physiological salt solution;

(iv) removal of the seaweed or kelp from the water and placing of pieces thereof on a flat surface;

(v) covering of the seaweed or kelp with absorbent or blotting material to remove excess water in the case of wakame or alternatively with a non-blotting material in the case of konbu; and (vi) compressing the seaweed or kelp into a flexible film.

The immersion in water may be for a period to allow absorption of water resulting in the seaweed or kelp attaining four or five times its original size. The immersion time may be of the order of 5–10 minutes.

The absorbent material for removal of excess water may be filter paper or blotting paper or cloth.

Compression of the blotted seaweed or kelp is for a suitable period resulting in a flexible film of between 0.01 to 0.2 mm uniform thickness. More preferably the flexible film is 0.1 mm uniform thickness. The compression may be carried out with a board with a weight placed on top or other form of commercial fluid actuated pressing apparatus. The compression time may be 24 hours in the case of wakame or 20 minutes in the case of konbu.

Alternatively, the seaweed or kelp may be powdered, shredded and/or thinly sliced and used with an alginate binder in this form and/or with other ingredients such as gelatin, glycerine or other suitable filler and rolled prior to being compressed or otherwise processed into a flexible film, coating or sheet.

Alternatively, the seaweed or kelp may be processed into a paste prior to being compressed into a flexible film or sheet. The paste is formed by reducing the seaweed or kelp to a powder before mixing with sodium alginate solution and optionally with water based gelatin solution as a filler. The powdered seaweed or kelp is allowed to absorb the solution resulting in a paste.

The sodium alginate solution is most preferably a concentration of 0.2 to 0.3% in water. The gelatin solution more specifically is of the concentration of 50 parts water or 80 parts water to 1 part gelatin powder.

In another variation, the powdered seaweed or kelp may be mixed with the sodium alginate and optionally with gelatin filler and allowed to form a film on a screen, similar to a silk screen as used for printing, before being peeled off and compressed.

Alternatively small pieces or fine shreds of seaweed or kelp may be bound together to form a single flexible sheet by use of the binder.

Preferably the ash used to dry and preserve the seaweed or kelp is wood ash. However, ash from the burning of other suitable materials may be used.

The non-blotting material used to cover the seaweed or kelp may be any suitable impervious and non-absorbent sheet material.

Other variations to the invention include the hand-making of seaweed and/or kelp coated capsule by pressing the drug into a sheet of seaweed and/or kelp laid over a heavily recessed mould such as a dish, funnel or hole in a board.

The drug, in the form of a powder or paste, is pressed lightly into the mould and the neck of the capsule is closed. The neck of the capsule is then sealed with sodium alginate solution.

Preferably an amount of barium sulfate or similar acid resistant essentially inert bulking agent that is non-toxic to humans may be added to the seaweed or kelp. Preferably 2–50% and more preferably 6–30% of bulking agent may be added. The addition of the bulking agent provides improved resistance to moisture. The addition of gelatin has a similar effect but it is not as satisfactory as barium sulfate. This enables the seaweed or kelp preparation to be less affected by humidity.

According to another aspect of the invention, there is disclosed an apparatus for forming a capsule as described above, said apparatus comprising:

(i) a base member having a concave surface;
(ii) a roller member attached to the base member and capable of reciprocatable movement thereto; and
(iii) a flexible belt rigidly attached to opposed ends of the base member in such a manner that the flexible belt is slackly supported on the concave surface and interposed between the roller member and the concave surface;

whereby a sheet formed from seaweed and/or kelp which is impervious to gastric acidity but denaturable by alkali formed in the intestines is initially supported on the flexible belt and subjected to a folding operation by movement of the roller member wherein adjacent parts of the sheet are bonded to each other by the use of binder applied to the sheet to enclose a drug within the sheet. Suitably the roller member is cylindrical.

BRIEF DESCRIPTION OF THE DRAWINGS

To enable the invention to be fully understood, reference will now be made to the accompanying drawings which show a preferred embodiment of the invention, wherein:

FIGS. 2A and 2B show an apparatus for encapsulating drugs; and

FIG. 2C shows a formed capsule according to the apparatus.

DETAILED DESCRIPTION

Figure 1A:
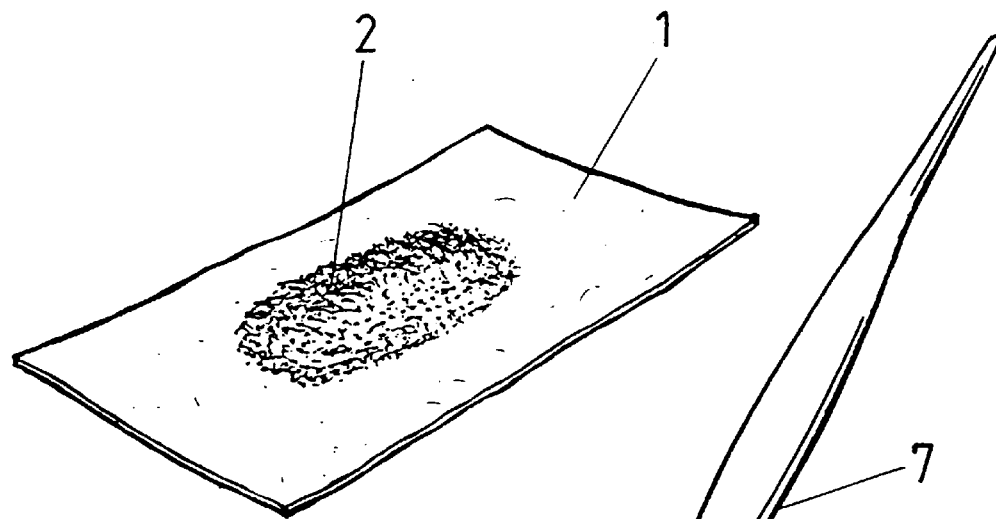
FIG. 1A shows drug on a sheet of seaweed and/or kelp.

In FIG. 1A is shown a sheet formed from seaweed and/or kelp 1 on which is placed drugs 2 for delivery to the intestines.

Figure 1B:
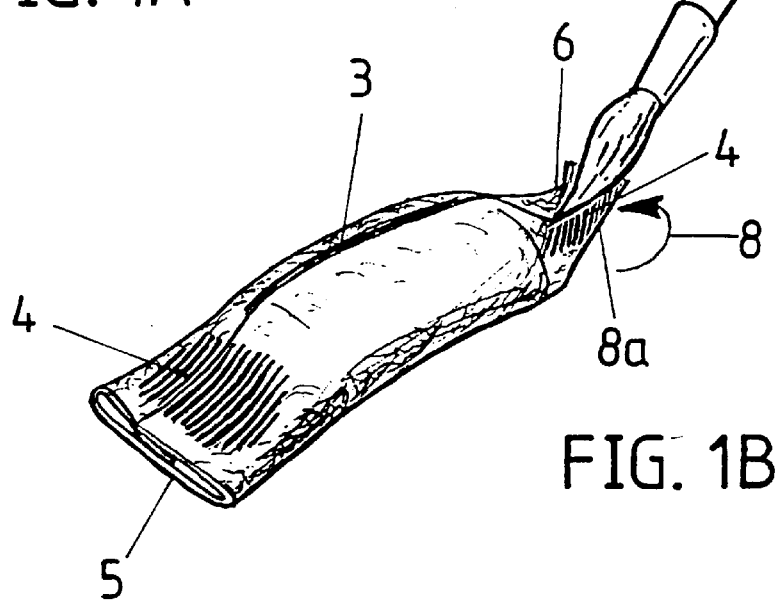
FIG. 1B shows binder solution being applied to a partially formed capsule.

In FIG. 1B, binder solution 4 is applied to both ends 5, 6 of the capsule 3 by means of a brush 7. The ends 5, 6 are then folded over in the direction of the arrow 8 resulting in a triangular configuration 8a. The ends 8a are then folded over resulting in a capsule 9 as shown in FIG. 1C.

Figure 1C:
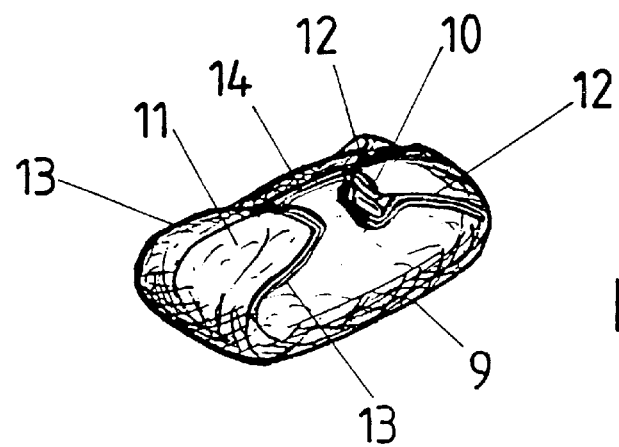
FIG. 1C shows a completely formed capsule.

FIG. 1C shows the capsule 9 in which the ends 10 and 11 have been folded over following the application of binder solution. Further binder solution is added to the edges 12, 13 and 14 to completely seal the package.

In FIGS. 2A and 2B, drugs 15 to be encapsulated are placed on sheet 16. Binder solution 17 according to the invention is applied along the free edges 18 of the wrapping material 16 by means of a brush 19.

By operation of a lever 20 in the direction 21 the cylindrical roller 22 is caused to roll in the direction 23. The lever 20 is pivotally connected to operating arms 20a and 20b which are pivotally attached to the base member 25 and cylindrical roller axle 22a at pivot point 20c and 20d respectively. The cylindrical roller axles 22a are located in slotted guides 22b (only one side shown for illustrative purposes). There is also shown a flexible belt 24 which is attached to base member 25 by fasteners 28 and in such a manner that it is slackly supported on concave surface 29 of base member 25.

In FIG. 2C is shown a cylindrical capsule 26 with crimped ends 27 formed as a result of operating the apparatus hereinbefore described and shown by FIGS. 2A and 2B.

Binder solution is applied to the crimped ends 27 to ensure that the capsule 26 is completely sealed.

The term "drug" as used herein includes vitamins, medicines, vaccines, proteins, food including health food or any other substance suitable for human or animal consumption. The drugs are not limited to solid pills or pellets but can extend to oil, wax or jelly-based drugs which are suspended, dissolved or otherwise carried in liquids.

In order to demonstrate the utility of the invention, the following experiments were conducted by the applicant in respect of capsules constructed in accordance with the invention from konbu or wakame and sodium alginate as a binder.

EXAMPLE 1

Immersion in fluid

| FLUID TESTED | RESULT |
| --- | --- |
| 10–20% Hydrochloric Acid | No effect |
| 20% acetic acid | No effect |
| Plum Vinegar | No effect after one week |
| Brewing Vinegar | No effect after one week |
| Artificial Stomach Acid | No effect after one week |

EXAMPLE 2

Immersion in artificial stomach acid for two hours prior to immersing in the following fluids

| FLUID TESTED | RESULT |
| --- | --- |
| Sodium Biocarbonate with pH 8.3 | Peels or breaks open within five minutes |
| Artificial Intestinal Fluid (pH 7.5) | Peels or breaks open within five minutes |

From the results obtained, it is shown that the capsules of the invention are impervious to acids inclusive of artificial stomach acids but breaks apart in alkali solutions such as artificial intestinal fluid.

EXAMPLE 3

In one form of manufacture of capsules in accordance with the invention, well dried, salted wakame or other suitable seaweed or kelp is processed into a powder of consistency of about 70–120 mesh by high speed grinding, blade slicer, ball mill or equivalent. This powder is then rinsed with water and adhesive such as sodium alginate (0.3%) is added and optionally an additional binder such as gelatin or glycerine is added. The wakame powder is then allowed to swell as it absorbs liquid. A layer of the thickened or swollen liquid or paste like material is then formed with the intention of forming a membrane. In this arrangement, a fine mesh screen on a frame (e.g. like a silk screen frame) is obtained, e.g. as used for hand crafting paper. This facilitates the production of a flat reconstituted seaweed-based membrane or film.

EXAMPLE 4

Powdered wakame of 70–120 mesh is obtained as described above in Example 3 and mixed with sodium alginate solution and further mixed with gelatin, glycerine or other binder that provides a suitable surface coating for a capsule containing a drug which has already been formed as described above.

EXAMPLE 5

The powdered wakame of 70–120 mesh prepared as described above in Example 3 is mixed with sodium alginate and also mixed with conventional raw materials used for making capsule shells such as glycerine, gelatin, pectins or other binder so as to produce a capsule shell component by a conventional process such as by moulding or extrusion. This shell component is then be combined with another shell component to provide a complete capsule with drug incorporated within the hollow interior of the completed shell. Calcium is then added to provide additional opacity if required.

EXAMPLE 6

A small amount of wakame that has been harvested and cleaned has been bagged in a damp state together with granules of salt which acts as a preserving agent. The wakame is washed to remove salt and other foreign matter and left standing in tepid or room temperature water for 5–10 minutes (approx.). The wakame absorbs water growing 4–5 times its original size. The wakame is removed and excess water drained off and subsequently placed within a cotton or nylon cloth and squeezed to obtain the slimy liquid extract which exists within. Viscosity between 1500–2000 centipores of the liquid extract is optimum.

6% by weight of barium sulfate is mixed with the extract. In this way, an exceedingly acid resistant and to some extent water resistant seaweed extract liquid coating material provided.

EXAMPLE 7

An extract prepared as described above in Example 6 is mixed with 30% by weight barium sulfate. Nine parts of the resulting liquid is then mixed with one part of melted gelatin (block or powder form) in a container jacketed in hot water. The resultant mix is poured out onto an easy-release flat surface such as Teflon PP or PE and dried in a refrigerator. The resultant thin sheet is impervious to acid but easily broken down by alkalis. This sheet then becomes the raw material for making capsules which possess the same excellent acid/alkali performance characteristics.

EXAMPLE 8

Two standard empty gelatin capsules are taken and 0.8 g of bifidus bacteria in powder form is placed in each capsule. One capsule is dipped in the liquid extract obtained from the procedure described in Example 6 (i.e. without the addition of barium sulfate). The other capsule is dipped in the liquid coating material also obtained from the procedure described in Example 6 (i.e. with barium sulfate). The two dipped capsules are then dried in a refrigerator for 10 hours. The resultant two coated capsules are then designated test capsule (1) and test capsule (2).

For the purpose of a batch test, six test capsules (1) and six test capsules (2) were prepared and subjected to the following tests:

|  | Artificial Stomach Acid | Artificial Intestinal Fluid |
| --- | --- | --- |
| Test Capsule (1) | all 6 unchanged after 1 hour | all 6 break up in 5 mins |
| Test Capsule (2) | all 6 unchanged after 2 hrs | all 6 break up in 5 mins |

EXAMPLE 9

Three test capsules (1) and three test capsules (2) were prepared as described above in Example 7. Each capsule were then placed in the following liquids and left for one hour, with regular agitation. Results are as shown:

| Acid Details | Test Capsule (1) | Test Capsule (2) |
| --- | --- | --- |
| 10% hydrochloric acid | not affected | not affected |
| 20% acetic acid | not affected | not affected |
| Artificial Stomach Fluid pH1.2 | not affected | not affected |

As shown above in regard to test capsules (1) and (2), when these capsules are placed in an acid environment, the coating material does not weaken but rather becomes stronger. Wakame is used as an ingredient in food is popular in Japan and its properties of becoming stronger when served with vinegar or other acidic liquids can easily be verified.

EXAMPLE 10

Test capsules (1) and (2) when placed in a water environment tend to swell or bloat out. Capsules (1) and (2), however, after soaking for one hour in an acid environment, if removed and cut open, exhibit a damp and flexible outer skin but the condition of the internal material within remains dry and unchanged. The condition and strength observed in regard to the outer skin suggests that the outer skin can comfortably resist acidity.

EXAMPLE 11

A selection of readily available overseas sourced (i.e. non-Japanese manufacture) medicines and health foods were obtained which included the following:
(a) elongated but rounded seamless capsules with soft skins which included royal jelly and liquid garlic extract);
(b) soft coatings obtained from tree resin which were used as a coating for liquid vitamin E; and
(c) solid tablets which included bifidus tablets.

Each health food (a), (b) and (c) were tested in artificial stomach acid of pH 1.2. Without exception, all broke down in 20 minutes or less. However, when coated with the liquid prepared as described above in Example 6, all these health foods survived more than one hour with ease in the same pH 1.2 environment. During these tests, it was established that ultimate survival times varied according to the properties of the surface coating, i.e. its absorption properties and the ability of the coating to adhere. Improved survival times could be improved by coating a second or even a third time.

EXAMPLE 12

The addition of barium sulfate also performs the excellent role of allowing the progress of coated capsules etc. to be accurately monitored within the body by means of x-ray photography.

In the first clinical trial of this technique, three capsules were loaded with powdered bifidus bacteria preparation, coated with the coating material prepared as described above in Example 6 and taken orally by a healthy patient on an empty stomach. X-ray photos were taken at the 3, 20, 30 and 60 minute marks, showing the capsules clearly and proving conclusively that the coating was working as expected. However, at between the 60 and 70 minute mark, each of the tablets passed into the opening of the small intestine, beginning to break down almost immediately, disappearing fully from the X-ray photos within minutes.

The performance of the coating of the invention, therefore, is ideal as a capsule or coating for oral usage, i.e. the coating survives an hour in stomach acid pH 1.2 but breaks down quickly in artificial intestinal fluid pH 6.8. To date, no known coating has come close to fulfilling these aims.

Advantages of the capsules or coatings of the present invention include the following:
(i) the use of seaweed makes a thin but exceedingly strong coating for a drug due to the fibrous or cellulosic value of the veins of seaweed leaves which are resistant to stomach acids such as dilute HCI but which readily breaks down in the alkaline conditions of the intestines.
(ii) the use of an alginate binder strongly resembles the alginate constituents of seaweed and thus the sealant soaks into the fibrous or cellulosic structure of the seaweed thereby facilitating strong bonding between seaweed pieces or shreds. A possible explanation for this is that cation exchange may occur between calcium ions in the seaweed and alkali metal ions found in the sealant.
(iii) the capsules due to their seaweed coating cannot be degraded due to excessively high temperatures and are readily transported down the intestinal tract and hence are subjected to the same absorption process as food particles;
(iv) the capsules are especially adapted for drugs that are designed to be broken down in the small intestine such as:
(a) bifudus bacteria which are normal flora of the small intestine but which reduce in adulthood rendering the small intestine to colitis infection;
(b) vitamins B1, B12, A and C, which require being absorbed through the intestines;
(c) ginseng;
(d) royal jelly; and
(e) vitamins and minerals which upon reaching the intestines reduce internal discomfort from disorders such as diahorrea and constipation.
(v) the capsules of the invention are extremely inexpensive to produce thereby providing substantive savings on raw material costs when compared to the prior art;
(vi) the capsules are formed from natural products which are part of the normal Japanese diet thereby substantially eliminating approval from pharmaceutical regulatory authorities such as the FDA;
(vii) the dosage of the drug which may be encapsulated by the capsules or coatings of the invention may be substantially reduced when compared to prior art capsules owing to the (a) improved resistance to stomach acids and (b) extreme durability in the intestines which properties are unique to the present invention; and
(viii) the capsule technology of the invention will dramatically reduce the cost of adminstration of vaccines. The capsules of the invention will allow the oral adminstration, in particular, of the synthetic vaccines based on peptides. It will therefore eliminate the need for injections and nurses and can be reduced to the administration of encapsulated pills only.

I claim:

1. An oral dosage form containing a drug for drug delivery incorporating a coating which comprises raw seaweed and/or kelp that contains absorbed water, and from which excess water has been removed, to form a film or liquid, which coating is impervious to gastric acidity but denaturable by alkali found in the intestines.

2. An oral dosage form as claimed in claim 1 wherein the seaweed and/or kelp is bound by binder.

3. An oral dosage form as claimed in claim 1 wherein a sheet is formed from seaweed and/or kelp to which a binder is added and subsequently the drug is retained within a capsule formed by a folding operation wherein adjacent parts of the sheet are bonded to each other by the binder.

4. An oral dosage form as claimed in claim 3 wherein the binder is a metal alginate.

5. An oral dosage form as claimed in claim 1 wherein the seaweed and/or kelp comprises a preparation of the genus laminaria known as "konbu" or "kombu" in Japanese or seaweed of the variety *undaria pinnatifada* also known as "wakame" in Japanese.

6. An oral dosage form as claimed in claim 5 wherein the seaweed and/or kelp is of the *shiraita konbu* variety.

7. An oral dosage form as claimed in claim 1 which is formed from kelps known as macrosystis or sarcophycus.

8. An oral dosage form as claimed in claim 2 wherein the binder is a metal alginate.

9. An oral dosage form as claimed in claim 8 wherein the binder is an alkali metal alginate.

10. An oral dosage form as claimed in claim 9 wherein the alginate is provided as a solution in water having a concentration of between 0.05% and 20% by weight in water.

11. An oral dosage form as claimed in claim 10 wherein the concentration is between 1% and 3% by weight in water.

12. An oral dosage form as claimed in claim 2 wherein the coating comprises a capsule which is formed from capsule components which incorporate at least some seaweed and/or kelp which also includes said binder.

13. An oral dosage form as claimed in claim 12 wherein the capsule is formed in one operation for encapsulation of liquid drugs.

14. An oral dosage form as claimed in claim 1 which also includes an amount of barium sulfate.

15. A method of drug delivery which includes the steps of:
 (i) coating a drug with raw seaweed and/or kelp which seaweed and/or kelp contains absorbed water, and from which seaweed and/or kelp excess water has been removed, to produce a film or liquid that is impervious to gastric acidity but denaturable by alkali found in the intestines; and (ii) administering the coated drug formed in step (i) to a subject orally.

16. A method as claimed in claim 15 wherein step (I) comprises encapsulating the drug with seaweed and/or kelp optionally incorporating a binder.

17. A method as claimed in claim 15 wherein step (I) comprises coating the drug with seaweed and/or kelp which also incorporates barium sulfate.

18. A method as claimed in claim 15 wherein step (I) comprises initially forming a sheet from seaweed and/or kelp and enclosing the drug within said sheet by a folding operation wherein adjacent parts of the sheet are bonded to each other.

19. An oral dosage form containing a drug for drug delivery incorporating a coating comprising raw seaweed and/or kelp containing absorbed water, and from which excess water has been removed to produce a film or liquid, which seaweed and/or kelp is selected from the group consisting of:

(i) a preparation of the genus laminaria known as "konbu" or "kombu" in Japanese, (ii) a seaweed of the variety *undaria pinnatifada* also known as "wakame" in Japanese, (iii) *shiraita kombu,* known in Japan as "white board kelp", and (iv) a family of kelps known as macrosystis or sarophycus.

* * * * *